United States Patent [19]

Frigerio et al.

[11] Patent Number: 4,988,713
[45] Date of Patent: Jan. 29, 1991

[54] 2-SELENOMETHYL-1,4-DIHYDROPYRIDINES HAVING CALCIUM-ANTAGONISTIC PROPERTIES AND PHARMACEUTICAL COMPOSITIONS CONTAINING THEM

[75] Inventors: Marco Frigerio; Carmelo A. Gandolfi; Odoardo Tofanetti; Sergio Tognella, all of Milan, Italy

[73] Assignee: Boehringer Biochemia Robin S.p.A., Milan, Italy

[21] Appl. No.: 404,069

[22] Filed: Sep. 7, 1989

Related U.S. Application Data

[63] Continuation of Ser. No. 199,234, May 27, 1988, abandoned.

[30] Foreign Application Priority Data

May 29, 1987 [IT] Italy .......................................... 20728

[51] Int. Cl.$^5$ .................. C07D 211/86; A61K 31/455
[52] U.S. Cl. ..................................... 514/356; 514/344; 514/352; 514/355; 546/321; 546/286; 546/312; 546/315
[58] Field of Search ............... 546/321, 286, 312, 315; 514/356, 344, 352, 355

[56] References Cited

U.S. PATENT DOCUMENTS 4,532,248 7/1985 Franckowiak et al. ............. 514/310

OTHER PUBLICATIONS

Goldmann et al., CA 104:109606u.

Primary Examiner—Jane T. Fan
Attorney, Agent, or Firm—Armstrong, Nikaido, Marmelstein, Kubovcik & Murray

[57] ABSTRACT

Compounds of formula I

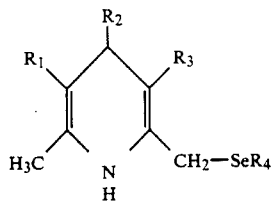

wherein
$R_1$ is a cyano, nitro, acetyl, benzoyl or alkoxycarbonyl group;
$R_2$ is an optionally substituted phenyl or heteroaryl group;
$R_3$ is an alkoxycarbonyl group;
$R_4$ is an alkyl group, optionally substituted by hydroxy, amino, phenyl, heterocyclic group; an optionally substituted phenyl group or an heterocyclic group.

Compounds I are useful in human therapy as agents able to interact with $CA^{++}$-dependent systems and as antitumor agents.

5 Claims, No Drawings

2-SELENOMETHYL-1,4-DIHYDROPYRIDINES HAVING CALCIUM-ANTAGONISTIC PROPERTIES AND PHARMACEUTICAL COMPOSITIONS CONTAINING THEM

This application is a continuation of application Ser. No. 199,234 filed May 27, 1988, now abandoned.

The present invention relates to 2-selenomethyl-1,4-dihydropyridines, to a process for the preparation thereof and to pharmaceutical compositions containing them.

The compounds of the invention have the following general formula I

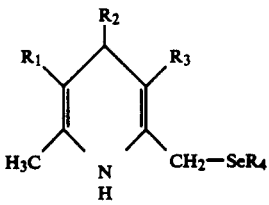

wherein
$R_1$ is a —COOR, acetyl, benzoyl, nitro or cyano group;
$R_2$ is a phenyl group, optionally substituted by one or more halogen atoms, nitro, cyano, $C_1$–$C_6$ alkyl, $C_1$–$C_6$ alkoxy, halo-$C_1$–$C_4$-alkoxy, $C_1$–$C_6$-alkylthio, $C_1$–$C_6$-alkylphenyl, $C_1$–$C_6$-alkoxycarbonyl groups or it represents an heteroaromatic 5 or 6-membered ring containing one or more heteroatoms selected from N, O and S;
$R_3$ is a COOR group;
$R_4$ is a $C_1$–$C_6$ alkyl group, optionally substituted by one or more hydroxy, amino, $C_2$–$C_6$-acylamino, monoalkylamino, dialkylamino, $C_1$–$C_4$-alkoxycarbonyl, phenyl, a 5 or 6-membered heterocyclic group containing one or more heteroatoms selected from N, O and S; a phenyl group optionally substituted by one or more halogen atoms, nitro, cyano, $C_1$–$C_6$-alkyl, $C_1$–$C_6$-alkoxy, halo-$C_1$–$C_4$-alkoxy, $C_1$–$C_6$-alkylthio, $C_1$–$C_6$-alkylphenyl, $C_1$–$C_6$-alkoxycarbonyl groups; a 5 or 6 membered saturated, unsaturated or a 5 or 6-membered aromatic heterocycle containing one or more heteroatoms selected from N, O and S; group of formula

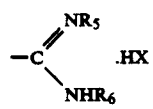

wherein X is a halogen atom and $R_5$ and $R_6$, which can be the same or different, are hydrogen, $C_1$–$C_6$-alkyl, benzyl or phenyl;
R is hydrogen, a $C_1$–$C_4$-alkyl group optionally substituted by hydroxy, $C_1$–$C_6$-alkoxy, amino, monoalkylamino, dialkylamino, phenyl groups.

The present invention further relates to the salts of compounds I with pharmaceutically acceptable acids or bases, and possible enantiomers, diastereoisomers and mixtures thereof.

Examples of heteroaromatic 5 or 6-membered rings/according to the invention comprise 2-, 3- or 4-pyridyl, 2- or 3-thienyl, 2- or 3-furyl, 2-thiazolyl, α-benzofuroxanyl groups.

Examples of monoalkylamino and dialkylamino groups according to the invention are methylamino, dimethylamino, ethylamino, diethylamino, isopropylamino, diisopropylamino, n-butylamino and the like.

Examples of saturated, unsaturated or aromatic heterocyclic rings according to the invention are pyrrolidin-1-yl, piperidin-1-yl, morpholin-4-yl, piperazin-1-yl, imidazol-1-yl, thiazol-2-yl, 2, 3- or 4-pyridyl, pyrrolidin-2-yl.

Preferred compounds according to the invention are those in which $R_1$ is a methoxycarbonyl, ethoxycarbonyl, isopropoxycarbonyl, methoxyethoxycarbonyl, nitro or cyano group; $R_2$ is phenyl, m-nitro-phenyl, m-chloro-phenyl, m-cyano-phenyl, o-nitro-phenyl, o-methylthiophenyl, m-methylthiophenyl group; $R_3$ is a methoxycarbonyl or ethoxycarbonyl group and $R_4$ is a phenyl, 2-aminoethyl or Se-$R_4$ is a selenoisouronium hydrochloride group.

The compounds of the invention are prepared by reacting compounds of general formula II:

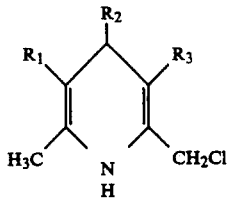

wherein $R_1$, R and $R_3$ have the above mentioned meanings; with a compound of general formula III:

wherein $R'_4$ has the above defined meanings, with the exception of group of formula

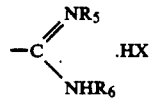

($R_5$, $R_6$ and X as above), and $M^+$ is the cation of an alkali or alkali-earth metal.

The reaction is carried out in inert solvents, such as lower alcohols, dioxane, tetrahydrofuran, 1,2-dimethoxyethane, chloroform, 1,2-dichloroethane or mixtures thereof, at a temperature from −20° C. to the reflux temperature of the solvent mixture, for reaction times from a few minutes to some hours.

The compounds of general formula III are preferably prepared in situ from compounds of general formula IV:

wherein $R'_4$ is as above defined, by reduction of the selenium-selenium bond; said reaction is carried out by known methods, in the same solvents above indicated, for example by reaction with reducing agents such as sodium borohydride, lithium borohydride, zinc borohydride, lithium alluminium hydride: the resulting solution of compound III is used as such for the reaction with compounds of formula II.

Compounds of formula II are disclosed in EP-A-0.212.340 in the Applicant's name.

Compounds of formula IV are known, easily available compounds.

Compounds of formula I in which R4 is an isouronium group are obtained by reaction of a compound of formula II with a compound of formula V:

wherein $R_5$ and $R_6$, which can be the same or different, are H, $C_1$–$C_6$ alkyl, benzyl or phenyl.

The reaction is carried out in inert solvents, such as lower alcohols, acetone, benzene, acetonitrile, dioxane, 1,2-dimethoxyethane, ethyl acetate, 1,2-dichloroethane and mixtures thereof, at a temperature from room temperature to the reflux temperature of the mixture, for times ranging from a few minutes to 24 hours.

Compounds of formula V are known in literature and easily available.

The further compounds of the invention proved to interact with $Ca^{++}$-dependent systems; particularly, they showed to have $Ca^{++}$-antagonistic action "in vitro" (test of rat aorta), and can displace 3H-nitrendipine from dihydropyridine receptor. Some of the compounds show anti-hypertensive activity, some other have protective action on the oxidative damages of the cell membranes while some other more are useful as anti-aging agents, i.e. they are able to counteract cellular aging process.

For the intended therapeutic uses, compounds of formula I are conveniently administered in form of parenteral or oral pharmaceutical compositions.

Examples of compositions for parenteral administration, particularly by intravenous or intraarterial route, are sterile aqueous solutions, sterile powders for extemporary preparation of a solution with a suited solvent, oily preparations for intramuscular or intraperitoneal administration.

Examples of compositions for oral administration comprise capsules, tablets, syrups, granulates and the like.

The compositions of the present invention are prepared by means of conventional techniques and excipients, such as those described in "Remington's Pharmaceutical Sciences Handbook", Hack Publishing Company, New York, U.S.A. The treatment Scheme, such as dosage, time, frequency of administration, use of particular therapeutic protocols, will depend on the severity of the pathology to be treated and on the conditions of the patient (weight, sex and age), and will be accordingly determined by the experts, according to well-established indications in medical practice.

The dosage will be comprised from 10 to 1.000 mg/day, optionally subdivided in more administrations.

The following examples further illustrate the invention without limiting it.

EXAMPLE 1

180 mg of sodium borohydride was added portionwise to a diphenyl diselenide (0.66 g) ethanolic solution (5 ml), kept under nitrogen at room temperature. After 30 minutes, the mixture was cooled and a 2-chloromethyl-3-carboethoxy-5-carbomethoxy-4-(m-nitrophenyl)-6-methyl-1,4-dihydropyridine (1,60 g) ethanol solution (10 ml) was dropped therein. The reaction mixture was stirred at 0° C. for 1 hour, kept to room temperature for 6 hours and neutralized with a monobasic sodium phosphate saturated solution, evaporated under vacuum to small volume, taken up in ethyl acetate (80 ml) and washed with water (3×50 ml). The organic layer was dried over sodium sulfate and evaporated under vacuum. After purification by column chromatography ($SiO_2$, eluent ethyl ether-ethyl acetate 80/20) 1.8 g of 2-phenylselenylmethyl-3-carboethoxy-5-carbomethoxy-4-(m-nitrophenyl)-6-methyl-1,4-dihydropyridine was obtained.

1H-NMR : ($CDCl_3$) δ: 1.00–1.20 (3H, t); 2.10(3H, s); 3.80(3H, s); 4.00–4.40(4H, m); 5.10(1H, s); 6.80(1H, m); 7.00–8.10(9H, m).

EXAMPLE 2

Using the appropriate 2-chloromethyl-1,4-dihydropyridines, under the above indicated conditions, the following compounds were obtained:

2-phenylselenylmethyl-3,5-dicarbomethoxy-4-phenyl-6-methyl-1,4-dihydropyridine;

2-phenylselenylmethyl-3,5-dicarboethoxy-4-(m-chlorophenyl)-5-methyl-1,4-dihydropyridine;

2-phenylselenylmethyl-3-carbomethoxy-4-(m-cyanophenyl)-5-isopropoxycarbonyl-6-methyl-1,4-dihydropyridine;

2-phenylselenylmethyl-3-carbethoxy-4-(o-nitrophenyl)-5-methoxy-ethoxycarbonyl-6-methyl-1,4-dihydropyridine;

2-phenylselenylmethyl-3-carboethoxy-4-(o-methylthiophenyl)-5-carbomethoxy-6-methyl-1,4-dihydropyridine;

2-phenylselenylmethyl-3,5-dicarbomethoxy-4-(m-methylthiophenyl)-6-methyl-1,4-dihydropyridine;

2-phenylselenylmethyl-3-carboethoxy-4-(m-nitrophenyl)-5-nitro-6-methyl-1,4-dihydropyridine;

2-phenylselenylmethyl-3-carboethoxy-5-carbomethoxy-4-(m-nitrophenyl)-6-methyl-1,4-dihydropyridine.

EXAMPLE 3

300 mg of $NaBH_4$ was added portionwise to a selenocystamine (320 mg) aqueous solution (3 ml), under nitrogen bubbling.

After about 1 hour, the yellow solution discolourized and, after dilution with ethanol (10 ml) and cooling to 0° C., a 2-chloromethyl-3-carboethoxy-5-carbomethoxy-4-(o-methylthiophenyl)-6-methyl-1,4-dihydropyridine (0.700 g) solution in ethanol (10 ml) was dropped therein.

The mixture was stirred at 0° C. for 2 hours, then at room temperature for a night, neutralized with a monobasic sodium phosphate saturated solution and evaporated under vacuum; the residue was treated with ethyl acetate (60 ml) and washed with water (5×20 ml). The organic layer was dried and concentrated under vacuum, the residue was purified by column chromatography ($SiO_2$, eluent chloroform-methanol-triethylamine 90/10/1).

0.8 g of 2-aminoethyl-selenylmethyl-3-carboethoxy-5-carbomethoxy-4-(o-methylthiophenyl)-6-methyl-1,4-dihydropyridine was obtained;

1H-NMR($CDCl_3$) - δ1.10–1.30(3H, t); 2.10(3H, s); 2.20–3.20(6H, m); 3.70(3H, m); 3.90–4.30(7H, m); 7.00–8.20(5H, m).

EXAMPLE 4

Operating under the same conditions of Example 3, the following compounds were obtained:

2-(2-aminoethyl)selenylmethyl-3,5-dicarbomethoxy-4(m-nitrophenyl)-6-methyl-1,4-dihydropyridine;
2-(2-aminoethyl)selenylmethyl-3-carbethoxy-4-(o-methylthiophenyl)-5-carbomethoxy-6-phenyl-1,4-dihydropyridine;
2-(2-aminoethyl)selenylmethyl-3,5-dicarboethoxy-4-(m-methylthiophenyl)-6-methyl-1,4-dihydropyridine;
2-(2-aminoethyl)selenylmethyl-3-carboethoxy-4-(m-nitrophenyl)-5-cyano-6-methyl-1,4-dihydropyridine;
2-(2-aminoethyl)selenylmethyl-3-carboethoxy-4-(m-methylthiophenyl)-5-nitro-6-methyl-1,4-dihydropyridine.

EXAMPLE 5

A solution of selenylurea (370 mg) and 2-chloromethyl-3,5-dicarboethoxy-4-(m-nitrophenyl)-6-methyl-1,4-dihydropyridine (1 g) in ethanol (25 ml) was refluxed for 2 hours under nitrogen atmosphere, thereafter solvent was evaporated to dryness, the residue was taken up into ethyl ether (50 ml) and the precipitated solid was filtered.

1.2 g of -[(6-methyl-3,5-dicarboethoxy-4-(m-nitrophenyl)-1,4-dihydropyridin-2-yl)methyl-]isoselenouronium chloride was obtained.

1H-NMR: (DMSO-d$_6$): δ1.00–1.30(6H, t); 2.20(3H, s); 3.80–4.20(4H, q); 4.50(2H, m); 5.00(1H, S); 7.10–8.10(5H, m); 8.50–10.00(4H, m).

EXAMPLE 6

Operating analogously to what described in Example 5, the following compounds were further obtained:
[(6-methyl-3-carboethoxy-4-(m-nitrophenyl)-5-carbomethoxy-1,4-dihydropyridin-2-yl)methyl-]isoselenouronium chloride;
[(6-methyl-3-carboethoxy-4-(o-methylthiophenyl)-5-carbomethoxy-1,4-dihydropyridin-2-yl)methyl-]isoselenouronium chloride;
[(6-methyl-3,5-dicarboethoxy-4-(m-methylthiophenyl)-1,4-dihydropyridin-2-yl)methyl]isoselenouronium chloride.

We claim:
1. A compound of formula I

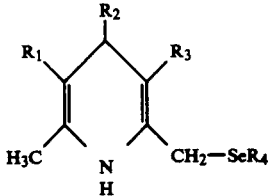

wherein:
R$_1$ is a —COOR, nitro or cyano group;
R$_2$ is a phenyl group, optionally substituted by a substituent selected from the group consisting of halogen atoms, nitro, and C$_1$–C$_6$-alkylthio;
R$_3$ is a COOR group;
R$_4$ is a C$_1$–C$_6$ alkyl group, optionally substituted by an amino group phenyl; or a group of the formula

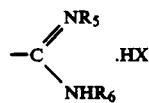

wherein X is a halogen atom and R$_5$ and R$_6$ are hydrogen; and
R is a C$_1$–C$_4$-alkyl group optionally substituted by a C$_1$–C$_6$-alkoxy group, an addition salt thereof with a pharmaceutically acceptable acid or base, an enantiomer, diastereoisomer or mixture thereof.

2. A compound as claimed in claim 1, wherein R$_4$ is a phenyl, 2-amino-ethyl, or isouronium hydrochloride group.

3. A compound as claimed in claim 1 or 2, wherein R$_2$ is selected from the group consisting of phenyl, m-nitrophenyl, o-methylthiophenyl, m-methylthiophenyl, m-chlorophenyl, and o-nitrophenyl.

4. A compound as claimed in claim 1, selected from the group consisting of:
(1) 2-phenylselenylmethyl-3,5-dicarbomethoxy-4-phenyl-6-methyl-1,4-dihydropyridine;
(2) 2-phenylselenylmethyl-3,5-dicarbomethoxy-4-(m-chlorophenyl)-5-methyl-1,4-dihydropyridine;
(3) 2-phenylselenymethyl-3-carboethoxy-4-(o-nitrophenyl)-5-methoxy-ethoxycarbonyl-6-methyl-1,4-dihydropyridine;
(4) 2-phenylselenylmethyl-3-carboethoxy-4-(o-methylthiophenyl)-5-carbomethoxy-6-methyl-1,4-dihydropyridine;
(5) 2-phenylselenylmethyl-3,5-dicarbomethoxy-4-(m-methylthio-phenyl)-6-methylthio-phenyl)-6-methyl-1,4-dihydropyridine;
(6) 2-phenylselenylmethyl-3-carboethoxy-4-(m-nitrophenyl)-5-nitro-6-methyl-1,4-dihydropyridine;
(7) 2-(2-aminoethyl)selenylmethyl-3,5-dicarbomethoxy-4-(m-nitropheny)-6-methyl-1,4-dihydropyridine;
(8) 2-(2-aminoethyl)selenylmethyl-3-carboethoxy-4-(o-methylthio-phenyl)-5-carbomethoxy-6-methyl-1,4-dihydropyridine;
(9) 2-(2-aminoethyl)selenylmethyl-3,5-dicarboethoxy-4-(m-methyl-thiophenyl)-6-methyl-1,4-dihydropyridine;
(10) 2-(-2-aminoethyl)selenylmethyl-3-carboethoxy-4-(m-nitro-phenyl)-5-cyano-6-methyl-1,4-dihydropyridine;
(11) 2-(2-aminoethyl)selenylmethyl-3-carboethoxy-4-(m-methylthio-phenyl)-5-nitro-6-methyl-1,4-dihydropyridine;
(12) [(6-methyl-3,5-dicarboethoxy-4-(m-nitrophenyl)-1,4-dihydropyridine-2-yl)methyl]isoselenouronium chloride;
(13) [(6-methyl-3-carboethoxy-4-(m-nitrophenyl)-5-carbomethoxy-1,4-dihydropyridin-2-yl)methyl-]isoselenouronium chloride;
(14) [(6-methyl-3-carboethoxy-4-(o-methylthiophenyl)-5-carbo-methoxy-1,4-dihydropyridin-2-yl)methyl-]isoselenouronium chloride;
(15) [(6-methyl-3,5-dicarboethoxy-4-(m-methylthiophenyl)-1,4-dihydropyridin-2-yl)methyl-]isoselenouronium chloride;
(16) 2-phenylselenylmethyl-3-carboethoxy-5-carbomethoxy-4-(m-nitrophenyl)-6-methyl-1,4-dihydropyridine;
(17) 2-(2-aminoethyl)selenylmethyl-3,5-dicarbomethoxy-4(m-nitrophenyl)-6-methyl-1,4-dihydropyridine;
(18) 2-(2-aminoethyl)selenylmethyl-3-carbomethoxy-6-phenyl-1,4-dihydropyridine;
(19) 2-(2-aminoethyl)selenylmethyl-3,5-dicarboethoxy-4(m-methyl-thiophenyl)-6-methyl-1,4-dihydropyridine;

(20) 2-(2-aminoethyl)selenymethyl-3-carboethoxy-4(m-nitropheny)-5-cyano-6-methyl-1,4-dihydropyridine; and

(21) 2-(2-aminoethyl)selenylmethyl-3-carboethoxy-4(m-methylthio-phenyl)-5-nitro-6-methyl-1,4-dihydropyridine.

5. A pharmaceutical composition for $Ca^{++}$-antagonistic therapy, comprising a $Ca^{++}$-antagonistic effective amount of a compound as claimed in any one of claims 1, 2 and 8, in admixture with a pharmaceutically acceptable carrier.

* * * * *